United States Patent [19]

Boon-Falleur et al.

[11] Patent Number: 5,747,271

[45] Date of Patent: May 5, 1998

[54] METHOD FOR IDENTIFYING INDIVIDUALS SUFFERING FROM A CELLULAR ABNORMALITY SOME OF WHOSE ABNORMAL CELLS PRESENT COMPLEXES OF HLA-A2/TYROSINASE DERIVED PEPTIDES, AND METHODS FOR TREATING SAID INDIVIDUALS

[75] Inventors: Thierry Boon-Falleur; Vincent Brichard; Aline Van Pel; Etienne De Plaen; Pierre Coulie; Jean-Christope Renauld, all of Brussels, Belgium; Thomas Wölfel, Mainz, Germany

[73] Assignee: Ludwig Institute For Cancer Research, New York, N.Y.

[21] Appl. No.: 636,676

[22] Filed: Apr. 23, 1996

Related U.S. Application Data

[62] Division of Ser. No. 295,227, Aug. 24, 1994, abandoned, which is a continuation of Ser. No. 994,928, Dec. 22, 1992, abandoned.

[51] Int. Cl.$^6$ .................. G01N 33/53; G01N 33/566; G01N 33/567; C12N 5/08

[52] U.S. Cl. .................. 435/7.24; 424/93.71; 435/2; 435/7.1; 435/7.23; 435/7.2; 435/325; 435/372.3; 435/183; 435/189; 436/503; 436/501; 436/813

[58] Field of Search .................. 424/93.71; 435/2, 435/7.1, 7.23, 7.24, 240.1, 240.2, 7.2, 325, 372.3, 183, 189; 436/503, 501, 813; 530/350, 328

[56] References Cited

PUBLICATIONS

Dermer, Bio/Technology, vol. 12, p. 320, 1994.
Boon, Int. J. Cancer, vol. 54, pp. 177–180, 1993.
Hodes, "Chapter 20", from: Fundamental Immunology, Second Edition, Ed. W.E. Paul, Raven Press, 1989, pp. 606 and 618.

*Primary Examiner*—Ronald B. Schwadron
*Attorney, Agent, or Firm*—Felfe & Lynch

[57] ABSTRACT

The invention relates to the identification of complexes of HLA-A2 and tyrosinase derived peptides on the surfaces of abnormal cells. The therapeutic and diagnostic ramifications of this observation are the subject of the invention.

2 Claims, 6 Drawing Sheets

METHOD FOR IDENTIFYING INDIVIDUALS SUFFERING FROM A CELLULAR ABNORMALITY SOME OF WHOSE ABNORMAL CELLS PRESENT COMPLEXES OF HLA-A2/TYROSINASE DERIVED PEPTIDES, AND METHODS FOR TREATING SAID INDIVIDUALS

This application is a Divisional of Ser. No. 08/295,227 filed Aug. 24, 1994, (now abandoned) which in turn is a continuation of Ser. No. 07/994,928, filed Dec. 22, 1992 (abandoned).

FIELD OF THE INVENTION

This invention relates to various therapeutic methodologies derived from the recognition that certain abnormal cells present complexes of HLA-A2 and peptides derived from tyrosinase on their surfaces. In addition, it relates to the ability to identify those individuals diagnosed with conditions characterized by cellular abnormalities whose abnormal cells present this complex.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., Advanced Immunology (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is present, but the T cell is not. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257:880 (1992); Fremont et al., Science 257:919 (1992); Matsumura et al., Science 257:927 (1992); Latron et al., Science 257:964 (1992).

The mechanism by which T cells recognize cellular abnormalities has also been implicated in cancer. For example, in PCT application PCT/US92/04354, filed May 22, 1992, published on Nov.26, 1992, and incorporated by reference, a family of genes is disclosed which are processed into peptides which, in turn, are expressed on cell surfaces. This can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35:145 (1992); van der Bruggen et al., Science 254:1643 (1991), for further information on this family of genes.

In U.S. patent application Ser. No. 07/938,334, now U.S. Pat. No. 5,405,940 the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBOJ 7:2715 (1988)). An early report on cDNA for the human enzyme is found in Kwon, U.S. Pat. No. 4,898,814. A later report by Bouchard et al., J. Exp. Med. 169:2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

None of these references teach or suggest, however, that tyrosinase may be treated in a manner similar to a foreign antigen or a TRAP molecule—i.e., it has now been found that in certain cellular abnormalities, such as melanoma, tyrosinase is processed and a peptide derived therefrom forms a complex with HLA-A2 molecules on certain abnormal cells. These complexes are recognized by cytolytic T cells ("CTLs"), which then lyse the presenting cells. The ramifications of this surprising and unexpected phenomenon are the subject of the invention, which is described in greater detail in the disclosure which follows.

DETAILED DESCRIPTION OF PREFERRED EMBODIMENTS

Example 1

Melanoma cell lines SK 29-MEL (also referred to in the literature as SK MEL-29) and LB24-MEL, which have been available to researchers for many years, were used in the following experiments.

Samples containing mononuclear blood cells were taken from patients AV and LB24-MEL (these patients were also the source of SK 29-MEL and LB24-MEL, respectively). The melanoma cell lines were contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS, and incubated for 45 minutes at 37° C. with 200 µCi/ml of Na($^{51}$Cr)O$_4$. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% of $CO_2$ atmosphere.

Plates were centrifuged again, and 100 ul aliquots of supernatant were collected and counted. Percentage of $^{51}$Cr release was calculated as follows:

$$\% \ ^{51}Cr \ release = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% TRITON X-100 to target cells.

Those mononuclear blood samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

These experiments led to isolation of CTL clone "IVSB" from patient AV and CTL clone 210/9 from patient LB24.

FIG. 1 presents the results of these assays, in panels A, B, G and I. Specifically, it will be seen that both CTLs lysed both melanoma cell lines, and that there was no lysis of the K562 and EBV-B cell lines.

Example 2

Figure 1A:
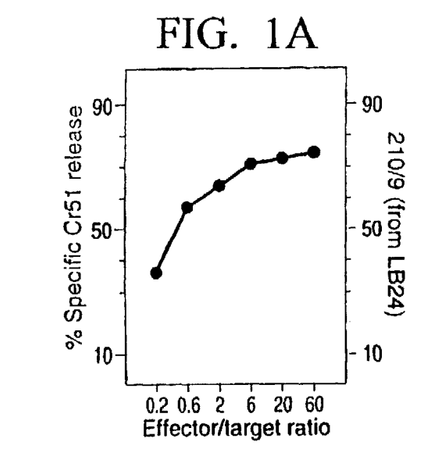
FIG. 1A shows lysis of cell line LB24.
Figure 1A:
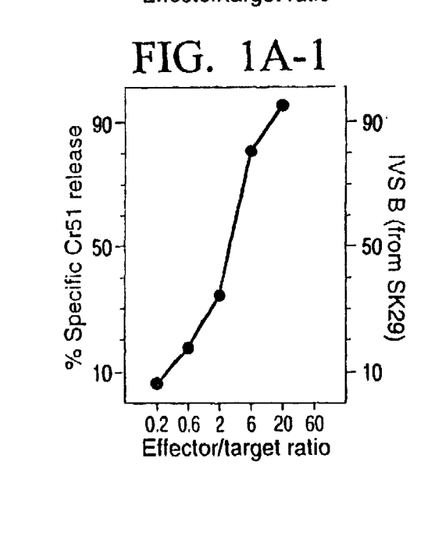
FIG. 1 describes, collectively, cell lysis studies. In particular.
FIG. 1B shows lysis of cell line SK29-MEL.
FIG. 1C shows lysis of cell line LB4.MEL.
FIG. 1D shows lysis of cell line SK23.MEL.
FIG. 1E shows lysis of cell line LE516.MEL.
FIG. 1F shows lysis studies on NK target K562.
FIG. 1G shows lysis of autologous, EBV-B transformed cells.
FIG. 1H shows lysis of the loss variant in FIG. 1F after transfection with a gene for HLA-A2.
FIG. 1I shows lysis of autologous IEBV-β transformed cells.
Figure 1B:
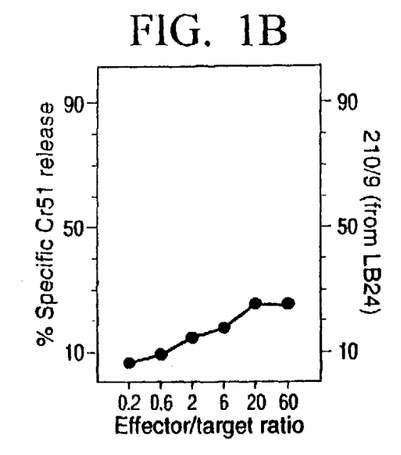
Figure 1B:
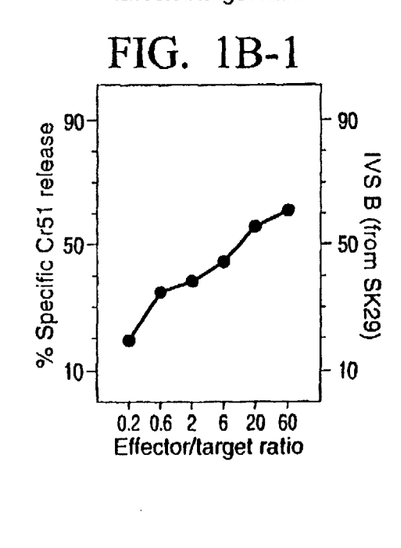
Figure 1C:
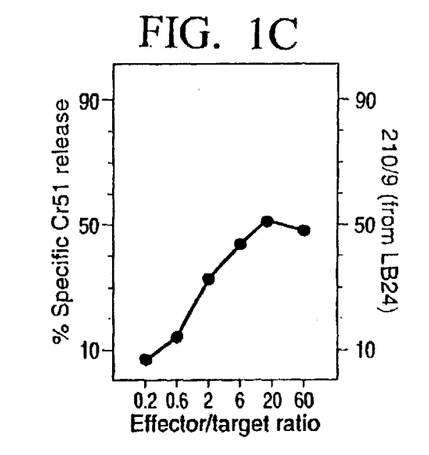
Figure 1C:
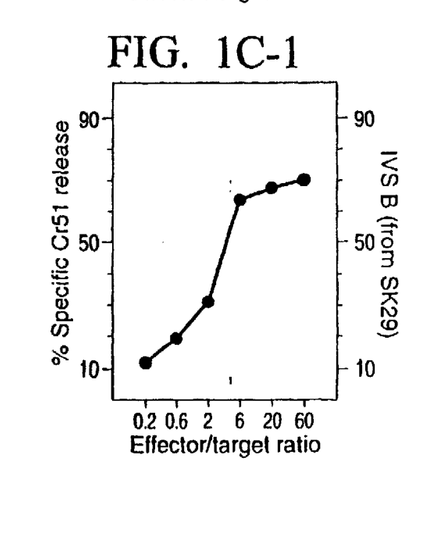
Figure 1D:
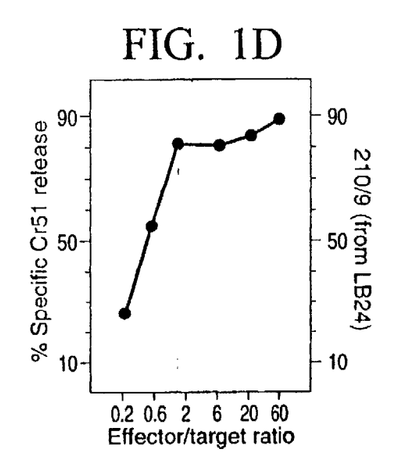
Figure 1D:
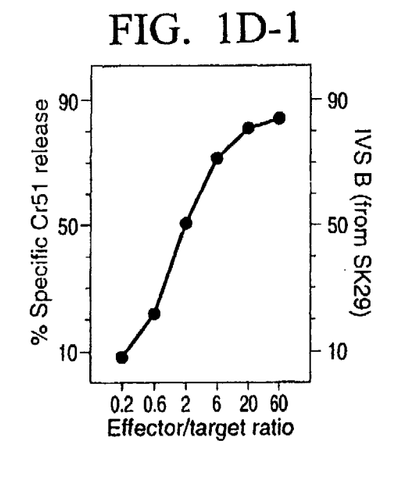
Figure 1E:
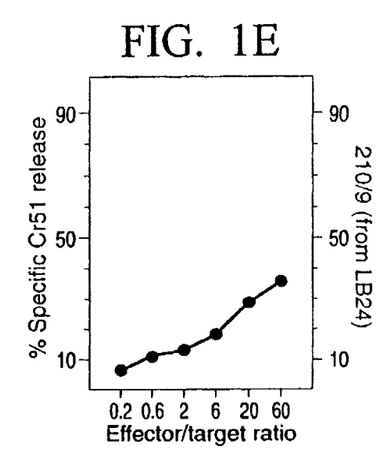
Figure 1E:
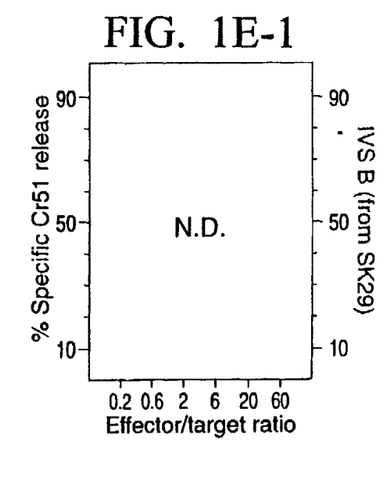

The CTLs described were tested against other melanoma cell lines to determine whether their target was shared by other melanoma cell lines. Lysis as described in Example 1 was studied for lines LB4.MEL, SK23.MEL (also known as SK MEL-23), and LE516.MEL. FIG. 1, panels C, D and E shows that the clones did lyse these lines.

Figure 1F:
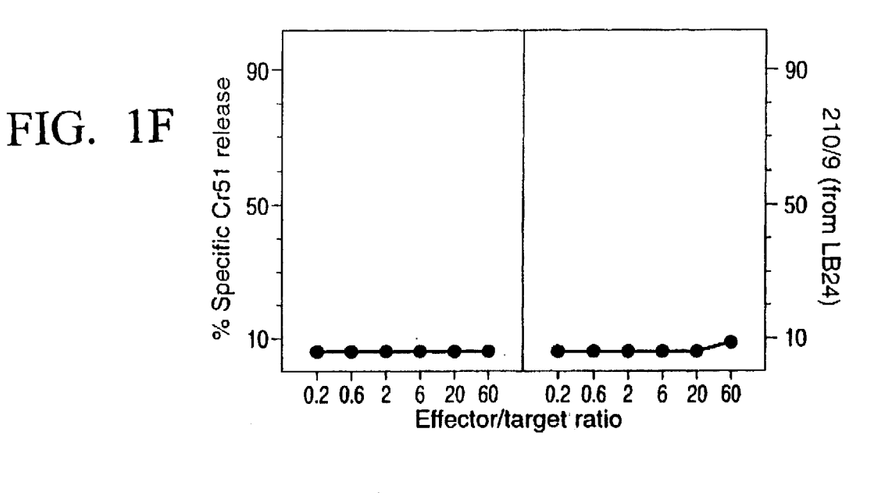
Figure 1F:
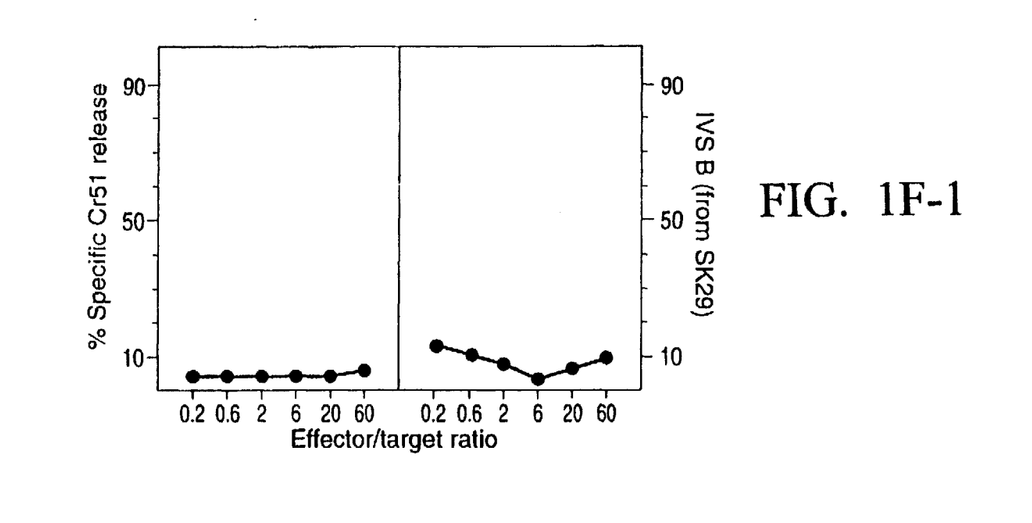
Figure 1G:
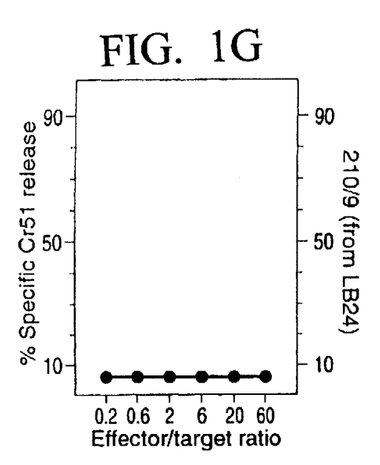
Figure 1G:
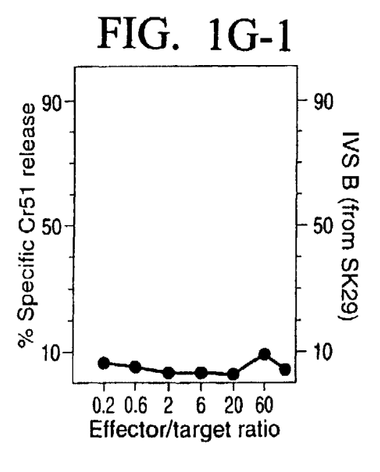
Figure 1H:
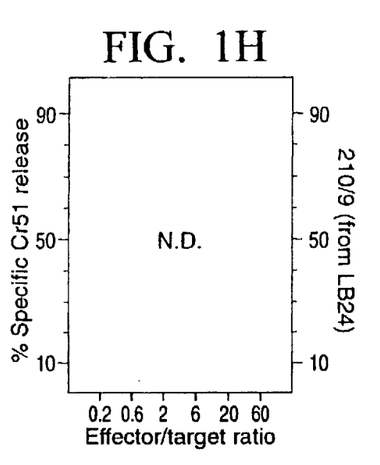
Figure 1H:
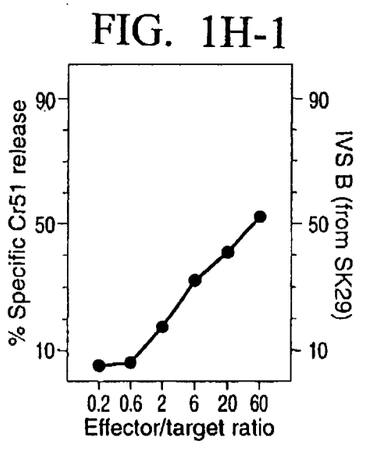
Figure 1I:
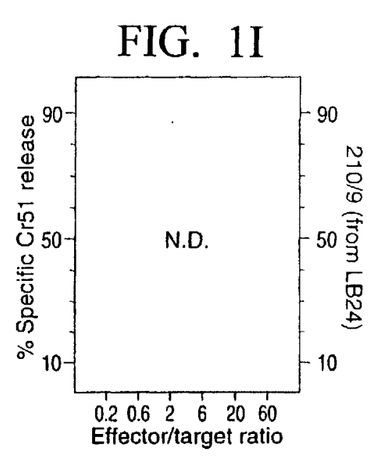
Figure 1I:
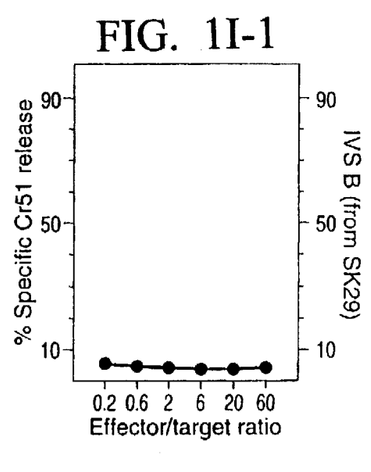

The tested lines are known to be of type HLA-A2, and the results suggested that the CTLs are specific for a complex of peptide and HLA-A2. This suggestion was verified by testing a variant of SK29-MEL which has lost HLA-A2 expression. FIG. 1, panel F shows these results. Neither clone lysed the HLA-loss variant. When the variant was transfected with the HLA-A2 gene of SK29-MEL, however, and retested, lysis was observed. Thus, it can be concluded that the presenting molecule is HLA-A2.

Example 3

Once the presenting HLA molecule was identified, studies were carried out to identify the molecule, referred to hereafter as the "tumor rejection antigen precursor" or "TRAP" molecule which was the source of the presented peptide.

To do this, total RNA was isolated from cell line SK29-MEL.1, which is a subclone of SK29-MEL. The RNA was isolated using an oligo-dT binding kit, following well recognized techniques. Once the total RNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electrophorated into JM101 *E. coli* (electroporation conditions: 1 pulse at 25 µfarads, 2500 V).

The transfected bacteria were selected with ampicillin (50 µg/ml), and then divided into 700 pools of 200 clones each. Each pool represented about 100 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

Example 4

The amplified plasmids were then transfected into eukaryotic cells. Samples of COS-7 cells were seeded, at 15,000 cells/well into tissue culture flat bottom microwells, in Dulbeco's modified Eagles Medium ("DMEM") supplemented with 10% fetal calf serum. The cells were incubated overnight at 37° C., medium was removed and then replaced by 30 µl/well of DMEM medium containing 10% Nu serum, 400 µg/ml DEAE-dextran, 100 µM chloroquine, 100 ng of plasmid pcDNA-I/Amp-A2 and 100 ng of DNA of a pool of the cDNA library described supra. Plasmid pcDNA-I/Amp-A2 contains the HLA-A2 gene from SK29-MEL. Following four hours of incubation at 37° C., the medium was removed, and replaced by 50 µl of PBS containing 10% DMSO. This medium was removed after two minutes and replaced by 200 µl of DMEM supplemented with 10% of FCS.

Following this change in medium, COS cells were incubated for 48 hours at 37° C. Medium was then discarded, and 2000 cells of either of the described CTL clones were added, in 100 µl of Iscove medium containing 10% pooled human serum. When clone 210/9 was used, the medium was supplemented with 25 U/ml of IL-2. Supernatant was removed after 24 hours, and TNF content was determined in an assay on WEHI cells, as described by Traversari et al., Immunogenetics 35:145–152 (1992), the disclosure of which is incorporated by reference.

Figure 2:
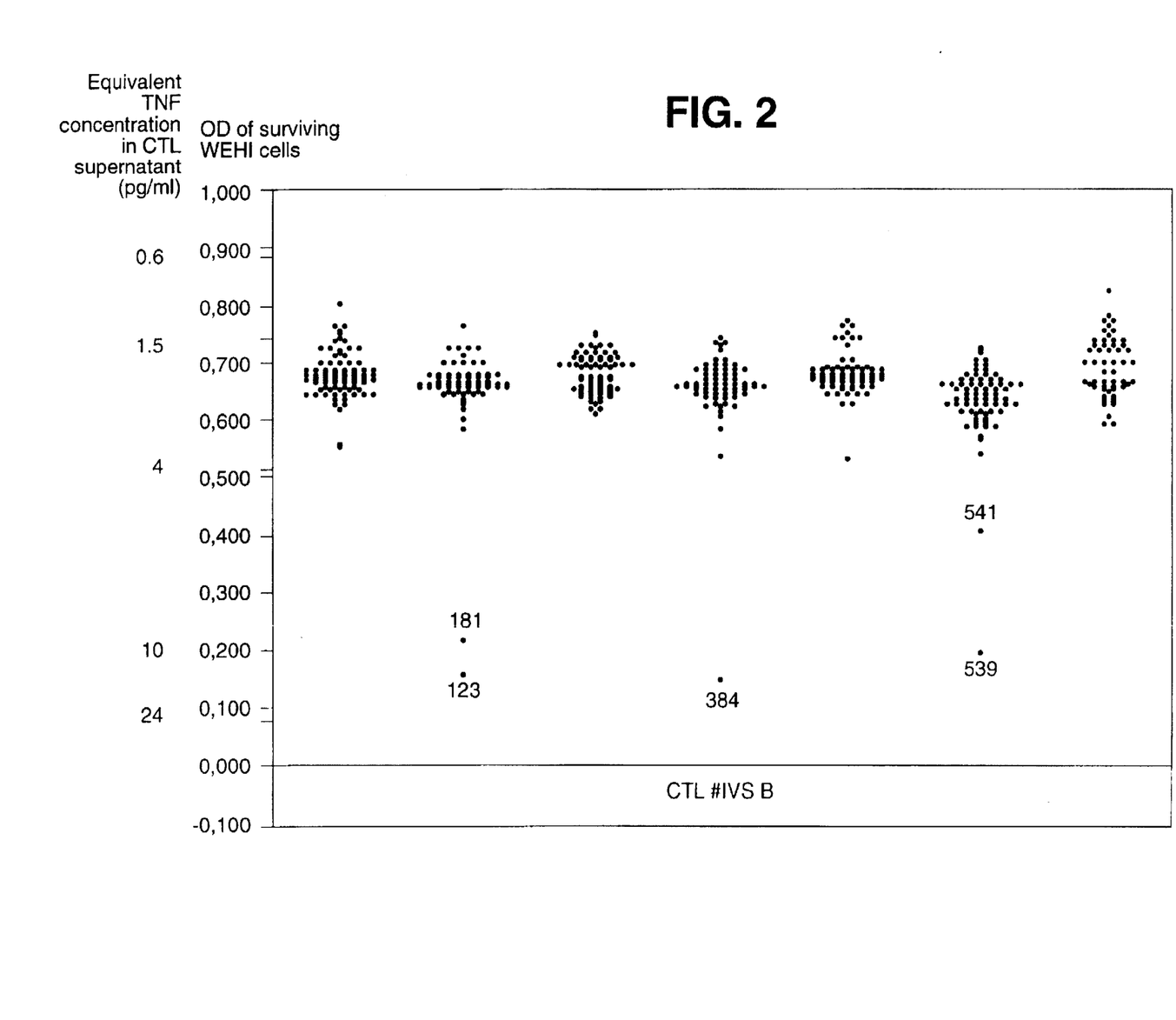
FIG. 2 presents studies of TNF release of CTL IVSB.
Figure 3:
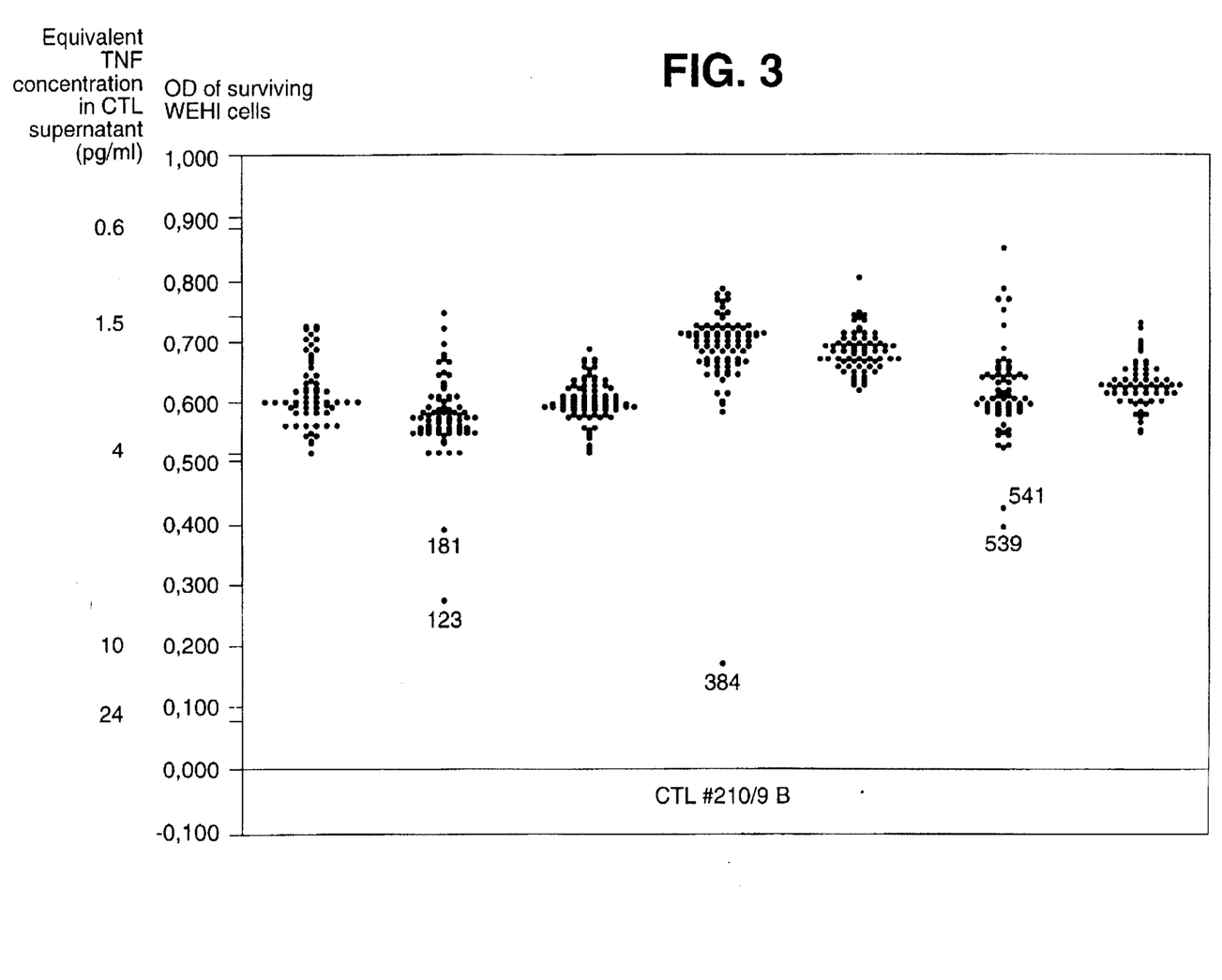
FIG. 3 depicts studies of TNF release of CTL 210/9.

Of 700 wells tested with IVSB, 696 showed between 0.6 and 4 pg of TNF per ml. The remaining four wells contained between 10 and 20 pg/ml of TNF. Homologous wells tested with CTL 210/9 showed similar, clearly higher values. FIGS. 2 and 3 present these data.

Example 5

Three of the four pools identified as high producers (numbers "123", "181" and "384") were selected for further experiments. Specifically, the bacteria were cloned, and 570 bacteria were tested from each pool. Plasmid DNA was extracted therefrom, transfected into a new sample of COS cells in the same manner as described supra, and the cells were again tested for stimulation of CTL 210/9 and CTL IVSB. A positive clone was found in pool 123 ("p123.B2"), and one was found in pool 384 ("p384.C6"). Convincing evidence that the transfected cells were recognized by CTLs was obtained by carrying out a comparative test of COS cells transfected with cDNA and the HLA-A2 gene, and COS cells transfected only with HLA-A2. TNF release in CTL supernatant was measured by testing it on WEHI cells. The optical density of the surviving WEHI cells was measured using MTT. Results are presented in Table 1:

TABLE 1

|       | cDNA (123.B2) + HLA-A2 DNA | no cDNA + HLA-A2 |
|-------|----------------------------|------------------|
| Run 1 | 0.087                      | 0.502            |
| Run 2 | 0.108                      | 0.562            |

The values for WEHI ODs' correspond to 24 pg/ml of TNF for cDNA and HLA-A2, versus 2.3 pg/ml for the control.

The plasmids from the positive clones were removed, and sequenced following art known techniques. A sequence search revealed that the plasmid insert was nearly identical to the cDNA for human tyrosinase, as described by Bouchard et al., J. Exp. Med. 169:2029 (1989), the disclosure of which is incorporated by reference. Thus, a normally occurring molecule (i.e., tyrosinase), may act as a tumor rejection antigen precursor and be processed to form a peptide tumor rejection antigen which is presented on the surface of a cell, in combination with HLA-A2, thereby stimulating lysis by CTL clones. The nucleic sequence of the identified molecule is presented as SEQ ID NO: 1.

The foregoing experiments demonstrate that, surprisingly, tyrosinase is processed as a tumor rejection antigen precursor, leading to formation of a complex of the resulting peptide with an HLA-A2 molecule on at least some abnormal cells, for example, melanoma cells with an HLA-A2 phenotype. The complex can be recognized by CTLs, and the presenting cell lysed. This observation has therapeutic and diagnostic ramifications which are features of the invention. With respect to therapies, the observation that CTLs which are specific for abnormal cells presenting the aforementioned complex are produced, suggests various therapeutic approaches. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. So as to enable the artisan to produce these CTLs, vectors containing the genes of interest, i.e., pcDNA-1/Ampl (HLA-A2), and p123.B2 (human tyrosinase), have been deposited in accordance with the Budapest Treaty at the Institut Pasteur, under Accession Numbers I1275 and I1276, respectively. COS cells, such as those used herein are widely available, as are other suitable host cells.

To detail the therapeutic methodology, referred to as adoptive transfer (Greenberg, J. Immunol. 136(5):1917 (1986); Reddel et al., Science 257:238 (Jul. 10, 1992); Lynch et al., Eur. J. Immunol. 21:1403–1410 (1991); Kast et al., Cell 59:603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA-A2/tyrosinase derived peptide complex. This can be determined very easily. For example CTLs are identified using the transfectants discussed supra, and once isolated, can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression of tyrosinase via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88:110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining tyrosinase itself with an adjuvant to facilitate incorporation into HLA-A2 presenting cells. The enzyme is then processed to yield the peptide partner of the HLA molecule.

The foregoing discussion refers to "abnormal cells" and "cellular abnormalities". These terms are employed in their broadest interpretation, and refer to any situation where the cells in question exhibit at least one property which indicates that they differ from normal cells of their specific type. Examples of abnormal properties include morphological and biochemical changes, e.g. Cellular abnormalities include tumors, such as melanoma, autoimmune disorders, and so forth.

The invention also provides a method for identifying precursors to CTL targets. These precursors are referred to as tumor rejection antigens when the target cells are tumors, but it must be pointed out that when the cell characterized by abnormality is not a tumor, it would be somewhat misleading to refer to the molecule as a tumor rejection antigen. Essentially, the method involves identifying a cell which is the target of a cytolytic T cell of the type discussed supra. Once such a cell is identified, total RNA is converted to a cDNA library, which is then transfected into a cell sample capable of presenting an antigen which forms a complex with a relevant HLA molecule. The transfectants are contacted with the CTL discussed supra, and again, targeting by the CTL is observed (lysis and/or TNF production). These transfectants which are lysed are then treated to have the cDNA removed and sequenced, and in this manner a precursor for an abnormal condition, such as a tumor rejection antigen precursor, can be identified.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
      ( A ) LENGTH: 1894 base pairs
      ( B ) TYPE: nucleic acid
      ( C ) STRANDEDNESS: single
      ( D ) TOPOLOGY: linear    ( x i ) SEQUENCE DESCRIPTION: SEQ ID NO: 1:

```
GGA  AGA  ATG  CTC  CTG  GCT  GTT  TTG  TAC  TGC  CTG  CTG  TGG  AGT  T
Gly  Arg  Met  Leu  Leu  Ala  Val  Leu  Tyr  Cys  Leu  Leu  Trp  Ser  P
-15            -10                      -5
ACC  TCC  GCT  GGC  CAT  TTC  CCT  AGA  GCC  TGT  GTC  TCC  TCT  AAG  A
Thr  Ser  Ala  Gly  His  Phe  Pro  Arg  Ala  Cys  Val  Ser  Ser  Lys  A
1               5                        10
ATG  GAG  AAG  GAA  TGC  TGT  CCA  CCG  TGG  AGC  GGG  GAC  AGG  AGT  C
Met  Gly  Lys  Glu  Cys  Cys  Pro  Pro  Trp  Ser  Gly  Asp  Arg  Ser  P
15              20                       25
GGC  CAG  CTT  TCA  GGC  AGA  GGT  TCC  TGT  CAG  AAT  ATC  CTT  CTG  T
Gly  Gln  Leu  Ser  Gly  Arg  Gly  Ser  Cys  Gln  Asn  Ile  Leu  Leu  S
35                   40                      45
GCA  CCA  CTT  GGG  CCT  CAA  TTT  CCC  TTC  ACA  GGG  GTG  GAT  GAC  C
Ala  Pro  Leu  Gly  Pro  Gln  Phe  Pro  Phe  Thr  Gly  Val  Asp  Asp  A
50                   55                      60
TCG  TGG  CCT  TCC  GTC  TTT  TAT  AAT  AGG  ACC  TGC  CAG  TGC  TCT  G
Ser  Trp  Pro  Ser  Val  Phe  Tyr  Asn  Arg  Thr  Cys  Gln  Cys  Ser  G
65                   70                      75
TTC  ATG  GGA  TTC  AAC  TGT  GGA  AAC  TGC  AAG  TTT  GGC  TTT  TGG  G
Phe  Met  Gly  Phe  Asn  Cys  Gly  Asn  Cys  Lys  Phe  Gly  Phe  Trp  G
80                   85                      90
AAC  TGC  ACA  GAG  AGA  CGA  CTC  TTG  GTG  AGA  AGA  AAC  ATC  TTC  G
Asn  Cys  Thr  Glu  Arg  Arg  Leu  Leu  Val  Arg  Arg  Asn  Ile  Phe  A
95                  100                     105
AGT  GCC  CCA  GAG  AAG  GAC  AAA  TTT  TTT  GCC  TAC  CTC  ACT  TTA  G
Ser  Ala  Pro  Glu  Lys  Asp  Lys  Phe  Phe  Ala  Tyr  Leu  Thr  Leu  A
115                 120                     125
CAT  ACC  ATC  AGC  TCA  GAC  TAT  GTC  ATC  CCC  ATA  GGG  ACC  TAT  G
His  Thr  Ile  Ser  Ser  Asp  Tyr  Val  Ile  Pro  Ile  Gly  Thr  Tyr  G
130                 135                     140
ATG  AAA  AAT  GGA  TCA  ACA  CCC  ATG  TTT  AAC  GAC  ATC  AAT  ATT  T
Met  Lys  Asn  Gly  Ser  Thr  Pro  Met  Phe  Asn  Asp  Ile  Asn  Ile  T
145                 150                     155
CTC  TTT  GTC  TGG  ATG  CAT  TAT  TAT  GTG  TCA  ATG  GAT  GCA  CTG  C
Leu  Phe  Val  Trp  Ile  His  Tyr  Tyr  Val  Ser  Met  Asp  Ala  Leu  L
160                 165                     170
GGA  TCT  GAA  ATC  TGG  AGA  GAC  ATT  GAT  TTT  GCC  CAT  GAA  GCA  C
Gly  Tyr  Glu  Ile  Trp  Arg  Asp  Ile  Asp  Phe  Ala  His  Glu  Ala  P
175                 180                     185
TTT  CTG  CCT  TGG  CAT  AGA  CTC  TTC  TTG  TTG  CGG  TGG  GAA  CAA  G
Phe  Leu  Pro  Trp  His  Arg  Leu  Phe  Leu  Leu  Arg  Trp  Glu  Gln  G
195                 200                     205
CAG  AAG  CTG  ACA  GGA  GAT  GAA  AAC  TTC  ACT  ATT  CCA  TAT  TGG  G
Gln  Lys  Leu  Thr  Gly  Asp  Glu  Asn  Phe  Thr  Ile  Pro  Tyr  Trp  A
210                 215                     220
CGG  GAT  GCA  GAA  AAG  TGT  GAC  ATT  TGC  ACA  GAT  GAG  TAC  ATG  G
Arg  Asp  Ala  Glu  Lys  Cys  Asp  Ile  Cys  Thr  Asp  Glu  Tyr  Met  G
225                 230                     235
CAG  CAC  CCC  ACA  AAT  CCT  AAC  TTA  CTC  AGC  CCA  GCA  TCA  TTC  T
Gln  His  Pro  Thr  Asn  Pro  Asn  Leu  Leu  Ser  Pro  Ala  Ser  Phe  P
240                 245                     250
TCT  TGG  CAG  ATT  GTC  TGT  AGC  CGA  TTG  GAG  GAG  TAC  AAC  AGC  C
Ser  Trp  Gln  Ile  Val  Cys  Ser  Arg  Leu  Glu  Glu  Tyr  Asn  Ser  H
255                 260                     265
TCT  TTA  TGC  AAT  GGA  ACG  CCC  GAG  GGA  CCT  TTA  CGG  CGT  AAT  C
Ser  Leu  Cys  Asn  Gly  Thr  Pro  Glu  Gly  Pro  Leu  Arg  Arg  Asn  P
```

```
275                             280                              285
AAC CAT GAC AAA TCC AGA ACC CCA AGG CTC CCC TCT TCA GCT G
Asn His Asp Lys Ser Arg Thr Pro Arg Leu Pro Ser Ser Ala A
290                             295                              300
GAA TTT TGC CTG AGT TTG ACC CAA TAT GAA TCT GGT TCC ATG G
Glu Phe Cys Leu Ser Leu Thr Gln Tyr Glu Ser Gly Ser Met A
305                             310                              315
GCT GCC AAT TTC AGC TTT AGA AAT ACA CTG GAA GGA TTT GCT A
Ala Ala Asn Phe Ser Phe Arg Asn Thr Leu Glu Gly Phe Ala S
320                             325                              330
CTT ACT GGG ATA GCG GAT GCC TCT CAA AGC AGC ATG CAC AAT G
Leu Thr Gly Ile Ala Asp Ala Ser Gln Ser Ser Met His Asn A
335                             340                              345
CAC ATC TAT ATG AAT GGA ACA ATG TCC CAG GTA CAG GGA TCT G
His Ile Tyr Met Asn Gly Thr Met Ser Gln Met Gln Gly Ser A
355                             360                              365
GAT CCT ATC TTC CTT CTT CAC CAT GCA TTT GTT GAC AGT ATT T
Asp Pro Ile Phe Leu Leu His His Ala Phe Val Asp Ser Ile P
370                             375                              380
CAG TGG CTC CAA AGG CAC CGT CCT CTT CAA GAA GTT TAT CCA G
Gln Trp Leu Arg Arg His Arg Pro Leu Gln Glu Val Tyr Pro G
385                             390                              395
AAT GCA CCC ATT GGA CAT AAC CGG GAA TCC TAC ATG GTT CCT T
Asn Ala Pro Ile Gly His Asn Arg Glu Ser Tyr Met Val Pro P
400                             405                              410
CCA CTG TAC AGA AAT GGT GAT TTC TTT ATT TCA TCC AAA GAT C
Pro Leu Tyr Arg Asn Gly Asp Phe Phe Ile Ser Ser Lys Asp L
415                             420                              425
TAT GAC TAT AGC TAT CTA CAA GAT TCA GAC CCA GAC TCT TTT C
Tyr Asp Tyr Ser Tyr Leu Gln Asp Ser Asp Pro Asp Ser Phe G
435                             440                              445
TAC ATT AAG TCC TAT TTG GAA CAA GCG AGT CGG ATC TGG TCA T
Tyr Ile Lys Ser Tyr Leu Gly Gln Ala Ser Arg Ile Trp Ser T
450                             455                              460
CTT GGG GCG GCG ATG GTA GGG GCC GTC CTC ACT GCC CTG CTG G
Leu Gly Ala Ala Met Val Gly Ala Val Leu Thr Ala Leu Leu A
465                             470                              475
CTT GTG AGC TTG CTG TGT CGT CAC AAG AGA AAG CAG CTT CCT G
Leu Val Ser Leu Leu Cys Arg His Lys Arg Lys Gln Leu Pro G
480                             485                              490
AAG CAG CCA CTC CTC ATG GAG AAA GAG GAT TAC CAC AGC TTG T
Lys Gln Pro Leu Leu Met Glu Lys Glu Asp Tyr His Ser Leu T
495                             500                              505
AGC CAT TTA
Ser His Leu
513
TAAAAGGCTT AGGCAATAGA GTAGGGCCAA AAAGCCTGAC CTCACTCTAA CT
TGTCCAGGTT CCCAGAGAAT ATCTGCTGGT ATTTTTCTGT AAAGACCATT TG
TAACCTAATA CAAAGTGTAG CCTTCTTCCA ACTCAGGTAG AACACACCTG TC
GCTGTTTTCA CTCAGCCCTT TTAACATTTT CCCCTAAGCC CATATGTCTA AG
GCTATTTGGT AATGAGGAAC TGTTATTTGT ATGTGAATTA AAGTGCTCTT AT
A
```

We claims:

1. Method for identifying a candidate for treatment with a therapeutic agent specific for complexes of HLA-A2 and a tyrosinase derived peptide, comprising:
   (i) contacting an abnormal cell sample from a subject with a cytolytic T cell specific for said complexes, and
   (ii) determining lysis of at least part of said abnormal cell sample as an indication of a candidate for said treatment.

2. Method for identifying an abnormal cell which presents a complex of HLA-A2/tyrosinase derived peptide on its surface comprising contacting a sample of abnormal cells with a cytolytic T cell specific for said complex and determining lysis of said abnormal cells as a determination of cells which present said complex.

* * * * *

UNITED STATES PATENT AND TRADEMARK OFFICE
Certificate

Patent No. 5,747,271                                                       Patented: May 5, 1998

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Thierry Boon-Falleur; Vincent Brichard; Aline Van Pel; Etienne De Plaen; Pierre Coulie; Jean-Christophe Renauld; Thomas Wolfel; and Alexander Knuth.

Signed and Sealed this First Day of February, 2000.

CHRISTINA CHAN
*Supervisory Patent Examiner*
Art Unit 1644